(12) United States Patent
Quisenberry et al.

(10) Patent No.: US 8,758,419 B1
(45) Date of Patent: Jun. 24, 2014

(54) CONTACT COOLER FOR SKIN COOLING APPLICATIONS

(75) Inventors: Tony Quisenberry, Highland Village, TX (US); Niran Balachandran, Lewisville, TX (US); Sam K. McSpadden, Austin, TX (US); Bob Blackwell, Colleyville, TX (US)

(73) Assignee: ThermoTek, Inc., Flower Mound, TX (US)

( * ) Notice: Subject to any disclaimer, the term of this patent is extended or adjusted under 35 U.S.C. 154(b) by 266 days.

(21) Appl. No.: 12/364,434

(22) Filed: Feb. 2, 2009

Related U.S. Application Data

(60) Provisional application No. 61/024,971, filed on Jan. 31, 2008.

(51) Int. Cl.
*A61F 7/00* (2006.01)

(52) U.S. Cl.
USPC .............................................. 607/104; 607/96

(58) Field of Classification Search
USPC ........ 607/104, 108–111, 114; 62/3.2; 601/15; 128/400
See application file for complete search history.

(56) References Cited

U.S. PATENT DOCUMENTS

| | | |
|---|---|---|
| 773,828 A | 11/1904 | Titus et al. |
| 2,110,022 A | 3/1938 | Kliesrath |
| 2,504,308 A | 4/1950 | Donkle, Jr. |
| 3,014,117 A | 12/1961 | Madding |
| 3,164,152 A | 1/1965 | Vere Nicoll |
| 3,345,641 A | 10/1967 | Jennings |
| 3,367,319 A | 2/1968 | Carter, Jr. |
| 3,548,809 A | 12/1970 | Conti Francesco |
| 3,608,091 A | 9/1971 | Olson et al. |
| 3,660,849 A | 5/1972 | Jonnes et al. |
| 3,736,764 A | 6/1973 | Chambers et al. |
| 3,738,702 A | 6/1973 | Jacobs |
| 3,744,053 A | 7/1973 | Parker et al. |
| 3,744,555 A | 7/1973 | Fletcher et al. |
| 3,862,629 A | 1/1975 | Rotta |
| 3,894,213 A | 7/1975 | Agarwala |
| 4,006,604 A | 2/1977 | Seff |
| 4,013,069 A | 3/1977 | Hasty |
| 4,029,087 A | 6/1977 | Dye et al. |
| 4,206,751 A | 6/1980 | Schneider |
| 4,224,941 A | 9/1980 | Stivala |
| 4,375,217 A | 3/1983 | Arkans |
| 4,402,312 A | 9/1983 | Villari et al. |

(Continued)

FOREIGN PATENT DOCUMENTS

| | | |
|---|---|---|
| CH | 670 541 | 6/1989 |
| DE | 35 22 127 | 1/1987 |

(Continued)

OTHER PUBLICATIONS

U.S. Appl. No. 12/730,060, Parish et al.

(Continued)

*Primary Examiner* — Laura Bouchelle

(74) *Attorney, Agent, or Firm* — Winstead PC

(57) ABSTRACT

A contact cooler for thermal conditioning a surface is disclosed. The contact cooler may include a temperature controller assembly with recirculating temperature controlled fluid for heating and/or cooling a surface of a patient in contact with a cooling head. The cooling head may be attached to a handle for manual manipulation thereof.

20 Claims, 11 Drawing Sheets

(56) References Cited

U.S. PATENT DOCUMENTS

| | | |
|---|---|---|
| 4,459,468 A | 7/1984 | Bailey |
| 4,459,822 A | 7/1984 | Pasternack |
| 4,471,787 A | 9/1984 | Bentall |
| 4,503,484 A | 3/1985 | Moxon |
| 4,547,906 A | 10/1985 | Nishida et al. |
| 4,597,384 A | 7/1986 | Whitney |
| 4,608,041 A | 8/1986 | Nielsen |
| D285,821 S | 9/1986 | Kneisley |
| D288,372 S | 2/1987 | Adams |
| 4,660,388 A | 4/1987 | Greene, Jr. |
| D295,897 S | 5/1988 | Thimm-Kelly |
| 4,741,338 A | 5/1988 | Miyamae |
| 4,821,354 A | 4/1989 | Little |
| 4,844,072 A | 7/1989 | French et al. |
| 4,884,304 A | 12/1989 | Elkins |
| 4,901,200 A | 2/1990 | Mazura |
| 4,911,231 A | 3/1990 | Horne et al. |
| 4,926,881 A | 5/1990 | Ichinomiya et al. |
| 4,962,761 A | 10/1990 | Golden |
| 4,969,881 A | 11/1990 | Viesturs |
| 4,979,375 A | 12/1990 | Nathans et al. |
| 4,989,589 A | 2/1991 | Pekanmaki et al. |
| 4,995,698 A | 2/1991 | Myers |
| 4,996,970 A | 3/1991 | Legare |
| 5,044,364 A | 9/1991 | Crowther |
| 5,051,562 A | 9/1991 | Bailey et al. |
| D320,872 S | 10/1991 | McCrane |
| 5,067,040 A | 11/1991 | Fallik |
| 5,080,089 A | 1/1992 | Mason et al. |
| 5,090,409 A | 2/1992 | Genis |
| 5,092,271 A | 3/1992 | Kleinsasser |
| 5,097,829 A * | 3/1992 | Quisenberry ................ 607/105 |
| 5,106,373 A | 4/1992 | Augustine et al. |
| 5,112,045 A | 5/1992 | Mason et al. |
| 5,117,812 A | 6/1992 | McWhorter |
| 5,125,238 A | 6/1992 | Ragan et al. |
| 5,165,127 A | 11/1992 | Nicholson |
| 5,179,941 A | 1/1993 | Siemssen et al. |
| 5,184,612 A | 2/1993 | Augustine |
| 5,186,698 A | 2/1993 | Mason et al. |
| 5,230,335 A | 7/1993 | Johnson, Jr. et al. |
| 5,232,020 A | 8/1993 | Mason et al. |
| 5,241,951 A | 9/1993 | Mason et al. |
| 5,243,706 A | 9/1993 | Frim et al. |
| 5,263,538 A | 11/1993 | Amidieu et al. |
| 5,285,347 A | 2/1994 | Fox et al. |
| D345,082 S | 3/1994 | Wenzl |
| D345,609 S | 3/1994 | Mason et al. |
| D345,802 S | 4/1994 | Mason et al. |
| D345,803 S | 4/1994 | Mason et al. |
| 5,300,101 A | 4/1994 | Augustine et al. |
| 5,300,102 A | 4/1994 | Augustine et al. |
| 5,300,103 A | 4/1994 | Stempel et al. |
| 5,303,716 A | 4/1994 | Mason et al. |
| 5,316,250 A | 5/1994 | Mason et al. |
| D348,106 S | 6/1994 | Mason et al. |
| 5,323,847 A | 6/1994 | Koizumi et al. |
| 5,324,319 A | 6/1994 | Mason et al. |
| 5,324,320 A | 6/1994 | Augustine et al. |
| D348,518 S | 7/1994 | Mason et al. |
| 5,330,519 A | 7/1994 | Mason et al. |
| 5,336,250 A | 8/1994 | Augustine |
| 5,343,579 A | 9/1994 | Dickerhoff et al. |
| 5,350,417 A | 9/1994 | Augustine |
| D351,472 S | 10/1994 | Mason et al. |
| 5,352,174 A | 10/1994 | Mason et al. |
| 5,354,117 A | 10/1994 | Danielson et al. |
| D352,781 S | 11/1994 | Mason et al. |
| 5,360,439 A | 11/1994 | Dickerhoff et al. |
| 5,370,178 A | 12/1994 | Agonafer et al. |
| 5,371,665 A | 12/1994 | Quisenberry et al. |
| D354,138 S | 1/1995 | Kelly |
| D357,747 S | 4/1995 | Kelly |
| 5,402,542 A | 4/1995 | Viard |
| 5,405,370 A | 4/1995 | Irani |
| 5,405,371 A | 4/1995 | Augustine et al. |
| 5,407,421 A | 4/1995 | Goldsmith |
| D358,216 S | 5/1995 | Dye |
| 5,411,494 A | 5/1995 | Rodriguez |
| 5,411,541 A | 5/1995 | Bell et al. |
| 5,417,720 A | 5/1995 | Mason |
| 5,440,450 A | 8/1995 | Lau et al. |
| 5,449,379 A | 9/1995 | Hadtke |
| 5,466,250 A | 11/1995 | Johnson, Jr. et al. |
| 5,496,262 A | 3/1996 | Johnson, Jr. et al. |
| 5,505,726 A | 4/1996 | Meserol |
| 5,507,792 A | 4/1996 | Mason |
| 5,509,894 A | 4/1996 | Mason et al. |
| 5,528,485 A | 6/1996 | Devilbiss et al. |
| 5,561,981 A | 10/1996 | Quisenberry et al. |
| 5,566,062 A | 10/1996 | Quisenberry et al. |
| D376,013 S | 11/1996 | Sandman et al. |
| 5,578,022 A | 11/1996 | Scherson et al. |
| 5,588,954 A | 12/1996 | Ribando et al. |
| 5,591,200 A | 1/1997 | Cone et al. |
| D380,874 S | 7/1997 | Caswell |
| 5,648,716 A | 7/1997 | Devilbiss et al. |
| D383,546 S | 9/1997 | Amis et al. |
| D383,547 S | 9/1997 | Mason et al. |
| D383,848 S | 9/1997 | Mason et al. |
| 5,662,695 A | 9/1997 | Mason et al. |
| 5,672,152 A | 9/1997 | Mason et al. |
| 5,675,473 A | 10/1997 | McDunn et al. |
| 5,682,748 A | 11/1997 | DeVilbiss et al. |
| 5,689,957 A | 11/1997 | DeVilbiss et al. |
| 5,690,849 A | 11/1997 | DeVilbiss et al. |
| 5,711,029 A | 1/1998 | Visco et al. |
| 5,711,155 A | 1/1998 | DeVilbiss et al. |
| D393,073 S | 3/1998 | Downing et al. |
| 5,731,954 A | 3/1998 | Cheon |
| 5,733,321 A | 3/1998 | Brink |
| D394,707 S | 5/1998 | Tsubooka |
| 5,755,755 A | 5/1998 | Panyard |
| 5,772,618 A | 6/1998 | Mason et al. |
| 5,782,780 A | 7/1998 | Mason et al. |
| 5,795,312 A | 8/1998 | Dye |
| 5,807,294 A | 9/1998 | Cawley et al. |
| 5,827,208 A | 10/1998 | Mason |
| 5,831,824 A | 11/1998 | McDunn et al. |
| D403,779 S | 1/1999 | Davis et al. |
| D404,490 S | 1/1999 | Tripolsky |
| D405,884 S | 2/1999 | Roper |
| 5,871,526 A | 2/1999 | Gibbs et al. |
| 5,890,371 A | 4/1999 | Rajasubramanian et al. |
| 5,901,037 A | 5/1999 | Hamilton et al. |
| 5,923,533 A | 7/1999 | Olson |
| 5,947,914 A | 9/1999 | Augustine |
| 5,980,561 A | 11/1999 | Kolen et al. |
| 5,989,285 A | 11/1999 | DeVilbiss et al. |
| 6,007,559 A | 12/1999 | Arkans |
| 6,055,157 A | 4/2000 | Bartilson |
| 6,058,010 A | 5/2000 | Schmidt et al. |
| 6,058,712 A | 5/2000 | Rajasubramanian et al. |
| 6,080,120 A | 6/2000 | Sandman et al. |
| D428,153 S | 7/2000 | Davis |
| D430,288 S | 8/2000 | Mason et al. |
| D430,289 S | 8/2000 | Mason et al. |
| 6,117,164 A | 9/2000 | Gildersleeve et al. |
| 6,125,036 A | 9/2000 | Kang et al. |
| 6,129,688 A | 10/2000 | Arkans |
| 6,135,116 A | 10/2000 | Vogel et al. |
| 6,176,869 B1 | 1/2001 | Mason et al. |
| 6,186,977 B1 | 2/2001 | Andrews et al. |
| 6,238,427 B1 | 5/2001 | Matta |
| 6,260,890 B1 | 7/2001 | Mason |
| 6,270,481 B1 | 8/2001 | Mason et al. |
| 6,295,819 B1 | 10/2001 | Mathiprakasam et al. |
| 6,305,180 B1 | 10/2001 | Miller et al. |
| 6,319,114 B1 | 11/2001 | Nair et al. |
| 6,352,550 B1 | 3/2002 | Gildersleeve et al. |
| 6,358,219 B1 | 3/2002 | Arkans |
| 6,368,592 B1 | 4/2002 | Colton et al. |
| 6,436,064 B1 | 8/2002 | Kloecker |
| 6,443,978 B1 | 9/2002 | Zharov |

(56) References Cited

U.S. PATENT DOCUMENTS

| | | |
|---|---|---|
| 6,462,949 B1 | 10/2002 | Parish, IV et al. |
| 6,468,237 B1 | 10/2002 | Lina |
| 6,508,831 B1 * | 1/2003 | Kushnir .................. 607/104 |
| D472,322 S | 3/2003 | Hoglund et al. |
| D473,315 S | 4/2003 | Miros et al. |
| D473,656 S | 4/2003 | Miros et al. |
| D473,948 S | 4/2003 | Elkins et al. |
| 6,551,264 B1 | 4/2003 | Cawley et al. |
| D474,544 S | 5/2003 | Hoglund et al. |
| 6,562,060 B1 | 5/2003 | Momtaheni |
| 6,596,016 B1 | 7/2003 | Vreman |
| 6,648,904 B2 * | 11/2003 | Altshuler et al. .............. 607/96 |
| D484,601 S | 12/2003 | Griffiths et al. |
| D484,602 S | 12/2003 | Griffiths et al. |
| 6,660,027 B2 | 12/2003 | Gruszecki et al. |
| 6,667,883 B1 | 12/2003 | Solis et al. |
| 6,675,072 B1 | 1/2004 | Kerem |
| D486,870 S | 2/2004 | Mason |
| 6,695,823 B1 | 2/2004 | Lina et al. |
| 6,719,713 B2 | 4/2004 | Mason |
| 6,719,728 B2 | 4/2004 | Mason et al. |
| 6,736,787 B1 | 5/2004 | McEwen et al. |
| D492,411 S | 6/2004 | Bierman |
| 6,775,137 B2 | 8/2004 | Chu et al. |
| D496,108 S | 9/2004 | Machin et al. |
| 6,789,024 B1 | 9/2004 | Kochan, Jr. et al. |
| 6,802,823 B2 | 10/2004 | Mason |
| D499,846 S | 12/2004 | Cesko |
| 6,834,712 B2 | 12/2004 | Parish et al. |
| 6,846,295 B1 | 1/2005 | Ben-Nun |
| 6,848,498 B2 | 2/2005 | Seki et al. |
| 6,855,158 B2 | 2/2005 | Stolpmann |
| 6,893,414 B2 | 5/2005 | Goble et al. |
| D506,553 S | 6/2005 | Tesluk |
| 6,935,409 B1 | 8/2005 | Parish IV et al. |
| 6,936,019 B2 | 8/2005 | Mason |
| D510,140 S | 9/2005 | Brown |
| 6,945,988 B1 | 9/2005 | Jones |
| D510,626 S | 10/2005 | Krahner et al. |
| D515,218 S | 2/2006 | McGuire et al. |
| D523,147 S | 6/2006 | Tesluk |
| 7,066,949 B2 | 6/2006 | Gammons et al. |
| 7,081,128 B2 | 7/2006 | Hart et al. |
| D533,668 S | 12/2006 | Brown |
| D551,351 S | 9/2007 | Silva |
| D551,352 S | 9/2007 | Frangi |
| 7,306,568 B2 | 12/2007 | Diana |
| 7,354,411 B2 | 4/2008 | Perry et al. |
| D568,482 S | 5/2008 | Gramza et al. |
| D569,985 S | 5/2008 | Ganapathy et al. |
| 7,427,153 B1 | 9/2008 | Jacobs et al. |
| 7,429,252 B2 | 9/2008 | Sarangapani |
| 7,484,552 B2 | 2/2009 | Pfahnl |
| 7,492,252 B2 | 2/2009 | Maruyama |
| D595,620 S | 7/2009 | Kingsbury |
| D601,707 S | 10/2009 | Chouiller |
| D608,006 S | 1/2010 | Avitable et al. |
| D612,947 S | 3/2010 | Turtzo et al. |
| D613,870 S | 4/2010 | Shust |
| 7,717,869 B2 | 5/2010 | Eischen, Sr. |
| D618,358 S | 6/2010 | Avitable et al. |
| D619,267 S | 7/2010 | Beckwith et al. |
| D620,122 S | 7/2010 | Cotton |
| D625,018 S | 10/2010 | Smith et al. |
| D626,241 S | 10/2010 | Sagnip et al. |
| D626,242 S | 10/2010 | Sagnip et al. |
| D626,243 S | 10/2010 | Sagnip et al. |
| D626,245 S | 10/2010 | Sagnip et al. |
| D627,896 S | 11/2010 | Matsuo et al. |
| D628,300 S | 11/2010 | Caden |
| D630,759 S | 1/2011 | Matsuo et al. |
| 7,871,387 B2 | 1/2011 | Tordella et al. |
| D631,971 S | 2/2011 | Turtzo et al. |
| D633,657 S | 3/2011 | Oban |
| D634,437 S | 3/2011 | Gramza et al. |
| D634,851 S | 3/2011 | Chiang |
| D635,266 S | 3/2011 | Chiang |
| D635,267 S | 3/2011 | Chiang |
| D636,497 S | 4/2011 | Giaccone |
| D638,950 S | 5/2011 | Janzon |
| D640,380 S | 6/2011 | Tweardy et al. |
| D640,381 S | 6/2011 | Tweardy et al. |
| D649,648 S | 11/2011 | Cavalieri et al. |
| 8,052,630 B2 | 11/2011 | Kloecker et al. |
| D655,420 S | 3/2012 | Bowles |
| D655,821 S | 3/2012 | Matsuo |
| D657,063 S | 4/2012 | Chiang |
| D660,438 S | 5/2012 | Kennedy et al. |
| D660,439 S | 5/2012 | Chen et al. |
| D663,850 S | 7/2012 | Joseph |
| D665,088 S | 8/2012 | Joseph |
| D665,470 S | 8/2012 | Galbraith |
| D666,258 S | 8/2012 | Campbell |
| D666,301 S | 8/2012 | Joseph |
| 8,449,483 B2 | 5/2013 | Eddy |
| 2001/0039439 A1 | 11/2001 | Elkins et al. |
| 2002/0116041 A1 | 8/2002 | Daoud |
| 2002/0143373 A1 | 10/2002 | Courtnage et al. |
| 2003/0050594 A1 | 3/2003 | Zamierowski |
| 2003/0083610 A1 | 5/2003 | McGrath et al. |
| 2003/0089486 A1 | 5/2003 | Parish et al. |
| 2003/0089487 A1 | 5/2003 | Parish, IV et al. |
| 2003/0127215 A1 | 7/2003 | Parish, IV et al. |
| 2003/0135252 A1 | 7/2003 | MacHold et al. |
| 2003/0163183 A1 | 8/2003 | Carson |
| 2003/0176822 A1 | 9/2003 | Morgenlander |
| 2004/0008483 A1 | 1/2004 | Cheon |
| 2004/0030281 A1 | 2/2004 | Goble et al. |
| 2004/0046108 A1 | 3/2004 | Spector |
| 2004/0054307 A1 | 3/2004 | Mason et al. |
| 2004/0068309 A1 | 4/2004 | Edelman |
| 2004/0068310 A1 | 4/2004 | Edelman |
| 2004/0099407 A1 | 5/2004 | Parish, IV et al. |
| 2004/0133135 A1 | 7/2004 | Diana |
| 2004/0186535 A1 | 9/2004 | Knowlton |
| 2004/0193218 A1 | 9/2004 | Butler |
| 2004/0210176 A1 | 10/2004 | Diana |
| 2004/0221604 A1 | 11/2004 | Ota et al. |
| 2004/0260231 A1 | 12/2004 | Goble et al. |
| 2005/0004636 A1 | 1/2005 | Noda et al. |
| 2005/0006061 A1 | 1/2005 | Quisenberry et al. |
| 2005/0033390 A1 | 2/2005 | McConnell |
| 2005/0039887 A1 | 2/2005 | Parish, IV et al. |
| 2005/0070828 A1 | 3/2005 | Hampson et al. |
| 2005/0070835 A1 | 3/2005 | Joshi |
| 2005/0133214 A1 | 6/2005 | Pfahnl |
| 2005/0143797 A1 | 6/2005 | Parish et al. |
| 2005/0177093 A1 | 8/2005 | Barry et al. |
| 2005/0182364 A1 | 8/2005 | Burchman |
| 2005/0256556 A1 | 11/2005 | Schirrmacher et al. |
| 2005/0274120 A1 | 12/2005 | Quisenberry et al. |
| 2005/0284615 A1 | 12/2005 | Parish et al. |
| 2006/0034053 A1 | 2/2006 | Parish et al. |
| 2006/0058714 A1 | 3/2006 | Rhoades |
| 2006/0116620 A1 | 6/2006 | Oyaski |
| 2006/0241549 A1 | 10/2006 | Sunnen |
| 2006/0276845 A1 | 12/2006 | George et al. |
| 2006/0282028 A1 | 12/2006 | Howard et al. |
| 2007/0032778 A1 | 2/2007 | Heaton et al. |
| 2007/0068651 A1 | 3/2007 | Gammons et al. |
| 2007/0112401 A1 | 5/2007 | Balachandran et al. |
| 2007/0118194 A1 | 5/2007 | Mason et al. |
| 2007/0129658 A1 | 6/2007 | Hampson et al. |
| 2007/0233209 A1 | 10/2007 | Whitehurst |
| 2007/0260162 A1 | 11/2007 | Meyer et al. |
| 2007/0282249 A1 | 12/2007 | Quisenberry |
| 2008/0058911 A1 | 3/2008 | Parish et al. |
| 2008/0064992 A1 | 3/2008 | Stewart et al. |
| 2008/0071330 A1 | 3/2008 | Quisenberry |
| 2008/0082029 A1 | 4/2008 | Diana |
| 2008/0103422 A1 | 5/2008 | Perry et al. |
| 2008/0132976 A1 | 6/2008 | Kane et al. |
| 2008/0249559 A1 | 10/2008 | Brown et al. |
| 2008/0319362 A1 | 12/2008 | Joseph |

(56) References Cited

U.S. PATENT DOCUMENTS

| | | |
|---|---|---|
| 2009/0069731 A1 | 3/2009 | Parish et al. |
| 2009/0109622 A1 | 4/2009 | Parish et al. |
| 2009/0149821 A1 | 6/2009 | Scherson et al. |
| 2009/0254160 A1 | 10/2009 | Shawver et al. |
| 2010/0010477 A1 | 1/2010 | Augustine et al. |
| 2010/0030306 A1 | 2/2010 | Edelman et al. |
| 2010/0081975 A1 | 4/2010 | Avitable et al. |
| 2010/0121230 A1 | 5/2010 | Vogel et al. |
| 2010/0137764 A1 | 6/2010 | Eddy |
| 2010/0145421 A1 | 6/2010 | Tomlinson et al. |
| 2010/0150991 A1 | 6/2010 | Bernstein |
| 2010/0249679 A1 | 9/2010 | Perry et al. |
| 2010/0249680 A1 | 9/2010 | Davis |
| 2011/0009785 A1 | 1/2011 | Meyer et al. |
| 2011/0034861 A1 | 2/2011 | Schaefer |
| 2011/0071447 A1 | 3/2011 | Liu et al. |
| 2011/0082401 A1 | 4/2011 | Iker et al. |
| 2011/0087142 A1 | 4/2011 | Ravikumar et al. |

FOREIGN PATENT DOCUMENTS

| | | |
|---|---|---|
| EP | 0 489 326 | 6/1992 |
| GB | 2373444 A | 9/2002 |
| SU | 689674 | 10/1979 |
| WO | WO-93/09727 | 5/1993 |
| WO | WO-00/40186 | 7/2000 |
| WO | WO-01/14012 A1 | 3/2001 |

OTHER PUBLICATIONS

U.S. Appl. No. 12/708,422, Balachandran et al.
U.S. Appl. No. 12/871,188, Parish et al.
U.S. Appl. No. 13/107,264, Quisenberry.
U.S. Appl. No. 13/962,994, Quisenberry.
Copenheaver, Blaine R., "International Search Report" for PCT/US2012/035096 as mailed Aug. 7, 2012, 3 pages.
U.S. Appl. No. 29/402,115, Quisenberry.
U.S. Appl. No. 29/397,856, Quisenberry.
U.S. Appl. No. 29/400,194, Quisenberry.
U.S. Appl. No. 29/400,202, Quisenberry.
U.S. Appl. No. 29/400,212, Quisenberry.
U.S. Appl. No. 13/796,139, Quisenberry.
Artikis, T., PCT International Preliminary Report on Patentability as mailed Jul. 29, 2005, (10 pgs).
Tom Lee, T.Y. et al; "Compact Liquid Cooling System for Small, Moveable Electronic Equipment", IEEE Transactions on Components, Hybrids, and Manufacturing Technology, Oct. 15, 1992, vol. 15, No. 5, pp. 786-793.
Copenheaver, Blaine R., "International Search Report" for PCT/US2007/022148 as mailed Apr. 2, 2008, 2 pages.
Young, Lee W., "International Search Report" for PCT/US07/08807 as mailed Mar. 3, 2008, (3 pages).
Mahmoud Karimi Azar Daryany, et al., "Photoinactivation of *Escherichia coli* and *Saccharomyces cerevisiae* Suspended in Phosphate-Buffered Saline-A Using 266- and 355-nm Pulsed Ultraviolet Light", Curr Microbiol, vol. 56, 2008, pp. 423-428.
J. Li, et al., "Enhanced germicidal effects of pulsed UV-LED irradiation on biofilms", Journal of Applied Microbiology, 2010, pp. 1-8.
Cyro/Temp Therapy Systems; Product News Catalogue; Jobst Institute, Inc., 6 pages (Copyright 1982).
Copenheaver, Blaine R., "International Search Report" prepared for PCT/US2013/030475 as mailed May 23, 2013, 3 pages.
Quisenberry, Tony, "U.S. Appl. No. 13/359,210", filed Jan. 26, 2012.
Quisenberry, Tony, "U.S. Appl. No. 13/558,615", filed Jul. 26, 2012.
Quisenberry, Tony, "U.S. Appl. No. 29/424,860", filed Jun. 15, 2012.
Quisenberry, Tony, "U.S. Appl. No. 13/456,410", filed Apr. 26, 2012.
U.S. Appl. No. 13/190,564, Quisenberry et al.
U.S. Appl. No. 14/062,428, Quisenberry.

\* cited by examiner

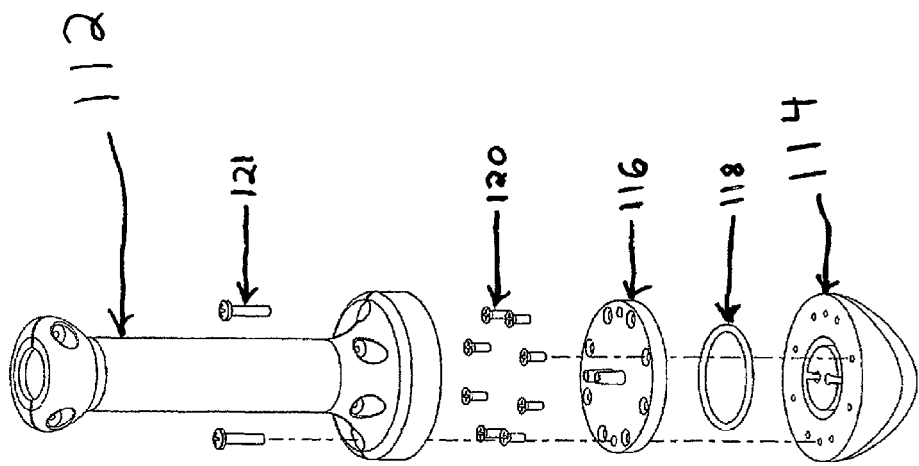

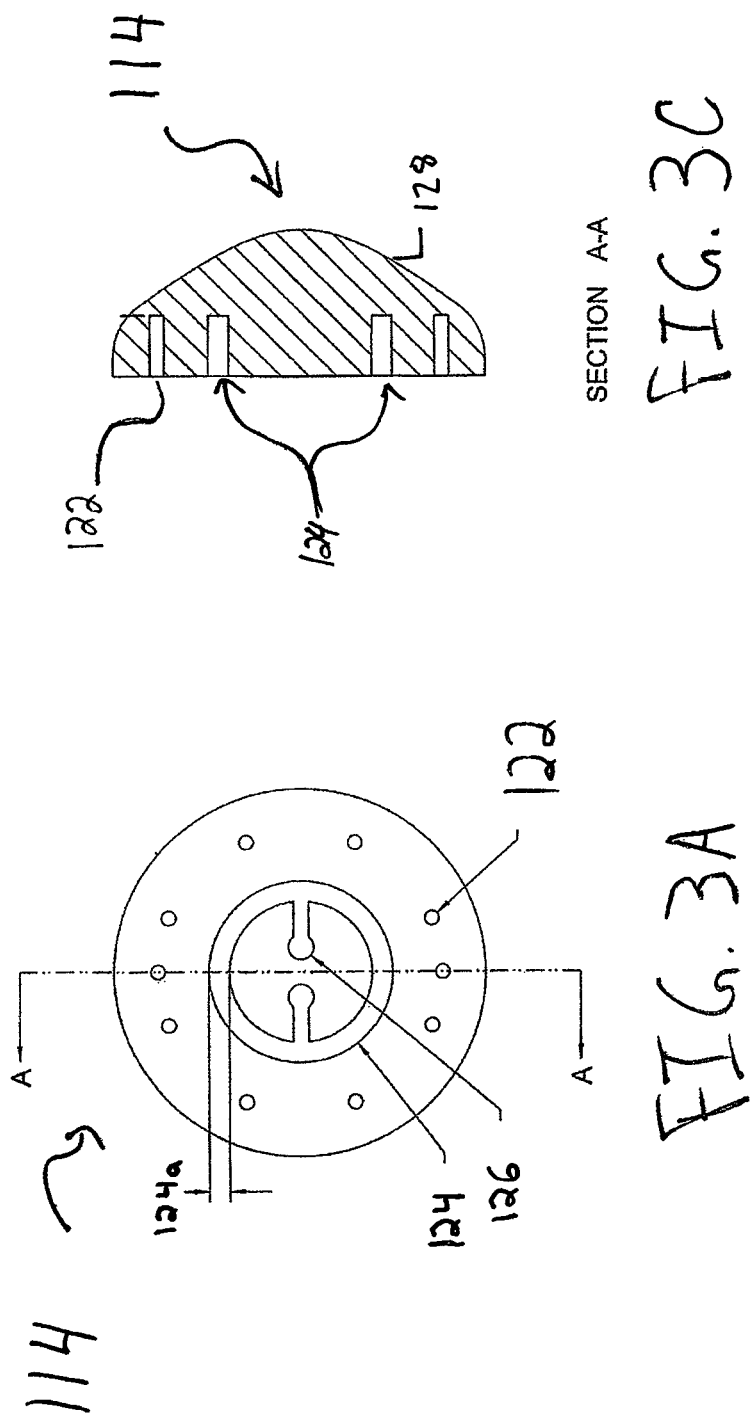

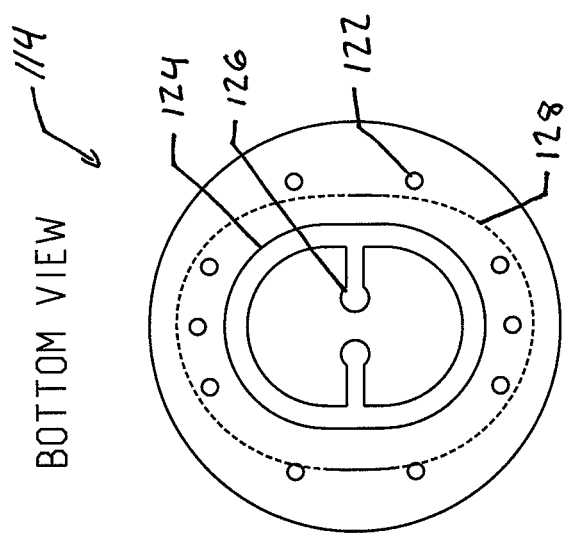

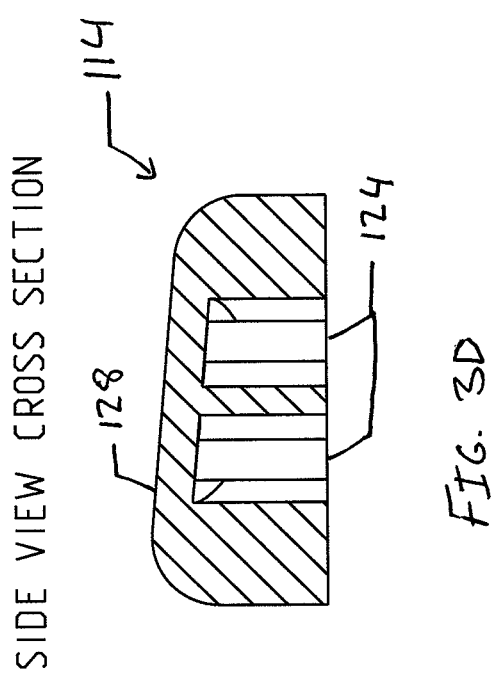

CONTACT COOLER FOR SKIN COOLING APPLICATIONS

RELATED APPLICATIONS

This application claims the benefit of, and incorporates by reference, U.S. Provisional Patent Application No. 61/024,971, filed Jan. 31, 2008.

TECHNICAL FIELD

The present invention relates in general to a system and method for temperature controlled coolers, and more particularly, but not by way of limitation, to temperature controlled contact coolers for selectively heating or cooling a skin surface.

BACKGROUND

Medical care providers recognize the need to provide warmth and cooling directly to patients as part of their treatment and therapy. For example, anesthetic properties have been reported using cold therapy for dermatology patients.

Conventional cooling technology typically includes passive cooling systems, compressor-based systems, and thermoelectric systems. In certain passive cooling systems, the air to be cooled is circulated over an air-to-air heat exchanger, which includes folded, finned heat exchangers, heat pipes, etc. The heat is then exchanged with the outside ambient air. As the amount of heat to be removed from the area increases, the size of the air-to-air heat exchanger increases. Compressor-based systems function by using a refrigerant and the cooling function is achieved by the compression and expansion of the refrigerant. Disadvantages of compressor-based systems include unwanted noise and vibration.

Thermoelectric temperature control systems use thermoelectric devices that pump heat using the Peltier effect. Typical thermoelectric devices incorporate a thermoelectric component utilizing electrical current to absorb heat from one side of the component and dissipate that heat on the opposite side. Thermal electric temperature control systems using thermal electric devices are, as described above, capable of both heating and cooling, low vibration, relatively high Coefficient Of Performance (ability to remove heat), low noise, and low profile.

It is known that dermal cooling may provide an analgesic effect such as a numbing of the surface of the skin to diminish pain caused by dermal procedures, such as, for example, laser or light-treatments and injections. To provide an analgesic effect by cooling a skin area, some approaches include the use of a cool object. Often the object is a piece of metal which has been placed first into a cooling medium, for example, a freezer or an ice bath before its use. Once the object has become sufficiently cold, the object may be removed from the cooling medium and placed on the skin surface to provide an analgesic effect. Such approaches have disadvantages. If these objects are cooled to temperatures below freezing to allow them to maintain temperatures below ambient for longer periods of time, problems may result from improper use. For example, one problem that may arise when temperatures below freezing are applied to a skin area is that cellular damage may occur.

Medical care providers thus recognize the need to provide carefully selected warmth and/or cooling directly to patients as part of their treatment and therapy. For example, anesthetic properties have been reported using cold therapy for dermatology patients. Several devices have been developed that deliver temperature controlled fluids and gasses to achieve various benefits. Typically, these devices have a heating or a cooling element, a pump for causing the air or fluid to flow, and a thermal interface between the patient and the temperature controlled fluid.

Other methods for cooling the temperature of a surface have been developed such as a roller with a cooling substance contained therein. Other pain management devices have used cooling devices that have a handle and a cooling head, where the handle contains a cooling substance to cool the head as it contacts a surface. Both pre-procedure and post-procedure dermal cooling has been utilized to protect the skin from damage from light sources used during such procedures as laser hair removal and skin peeling.

SUMMARY

In view of the foregoing and other considerations, the present invention relates to contact coolers for skin cooling applications.

Accordingly, a contact cooler is provided that may include a temperature controlled assembly with recirculating temperature controlled fluid for heating or cooling a surface of a patient in contact with the cooling head.

Another aspect of the present invention comprises a head with an input and an output for circulating a heat-transfer fluid therethrough. The head may be attached to a handle for manual manipulation of the cooling head. The input and output may be attached to a control unit. The control unit may increase or decrease the temperature of the circulating heat-transfer fluid depending on user inputted settings. The control unit may monitor the temperature of the exiting heat-transfer fluid and the returning heat-transfer fluid and may calculate the temperature at the cooling head based thereupon. The cooling head may be comprised of a thermally conductive material such as metal or other material that will transfer heat between the circulating heat-transfer fluid and the contact surface. In one embodiment, the material of the cooling head comprises stainless steel. In various embodiments, the handle may be formed from a thermal insulating material. In one embodiment, the handle comprises plastic.

In one embodiment, the cooling head is constructed with a plurality of distribution channels therein for circulation of the heat-transfer fluid therethrough. In various embodiments, a thin plastic or preferably latex-free cover is provided for placement between the cooling head and the surface to be cooled.

In one embodiment, the cooling head is constructed of one of a number of specific shapes facilitating the efficacy of use upon a patient.

The foregoing has outlined some of the features and technical advantages of the present invention in order that the detailed description of the invention that follows may be better understood. Additional features and advantages of the invention will be described hereinafter which form the subject of the claimed invention.

BRIEF DESCRIPTION OF THE DRAWINGS

The foregoing and other features and aspects of the present invention will be best understood with reference to the following detailed description of a specific embodiment of the invention, when read in conjunction with the accompanying drawings, wherein:

FIG. 2 is an exploded view of the contact cooling head of FIG. 1;

FIG. 3A is a top view of a portion of the contact cooling head of FIG. 1;

FIG. 3B is a bottom view of a portion of the contact cooling head of FIG. 1;

FIG. 3C is a sectional view of the contact cooling head of FIG. 3A along line A-A;

FIG. 3D is a sectional view of an additional embodiment of the contact cooling head of FIG. 3A along line A-A;

DETAILED DESCRIPTION

Figure 1:
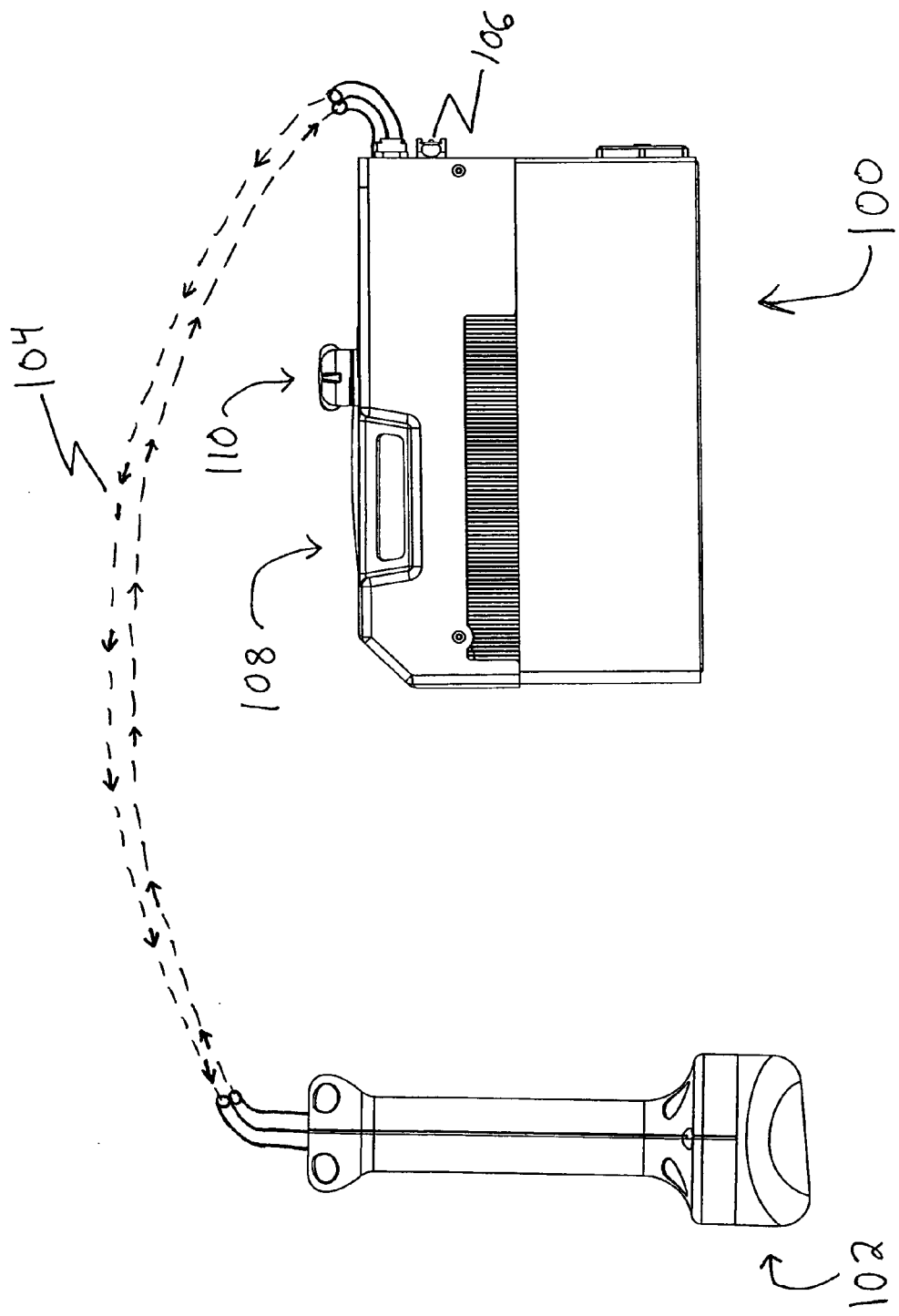
FIG. 1 is a side view of a contact cooling system incorporating a contact cooling head in accordance with certain aspects of the present invention.

Refer now to the drawings, wherein depicted elements are not necessarily shown to scale and wherein like or similar elements are designated by the same reference numeral through the several views. As used herein, the terms "up" and "down"; "upper" and "lower"; and other like terms indicating relative position to a given point or element are utilized to more clearly describe some elements of the embodiments of the invention. Commonly, these terms relate to a reference point as the skin surface of a patient. Also as used herein, the term "cooling head" includes the function of transferring heat either to or from a patient.

Referring now to FIG. 1, a temperature control unit 100 is shown in fluid communication with a contact cooler 102 via connection tubing 104. Connection tubing 104 has been cut away and circulation arrows have been drawn to show that the connection tubing, such as conduit, hose, pipe, or other tubing, can be of any length. The circulation arrows show that heat-transfer fluid flows to contact cooler 102 from control unit 100. The heat-transfer fluid then flows, in a closed loop, back from contact cooler 102 to control unit 100. In the embodiment shown, control unit 100 includes a front side with a user interface (not shown) and a back side with input and output ports 106 for the flow of heat-transfer fluid therethrough. It can also be seen that control unit 100 may have a handle 108 to facilitate use and mobility of the unit. Control unit 100 may also include a refill opening 110 disposed thereon for adding a heat-transfer fluid to a reservoir contained therein. While control unit 100 is shown having a particular size and shape, a chassis of any size or shape may be utilized for housing control unit 100.

Control unit 100 may be operable to adjust or maintain a temperature control fluid flowing therethrough. In various embodiments, control unit 100 may be operable to monitor various parameters of the heat-transfer fluid as it circulates through a closed loop. For example, a temperature and/or flow rate of the heat-transfer fluid may be monitored. As will be explained in more detail below, the various monitored parameters may be utilized to calculate the temperature at a head of contact cooler 102.

FIG. 2 is an exploded view of an embodiment of a contact cooler 102. In the embodiment shown, contact cooler 102 includes a handle 112 coupled to a cooling head 114 via a plurality of screws 121. Disposed between cooling head 114 and handle 112 is an attachment plate 116 having ports running therethrough. In some embodiments, attachment plate 116 may be coupled to cooling head 114 using a plurality of screws 120 and having an o-ring 118 disposed therebetween. As will be explained in more detail below, a heat-transfer fluid may flow from the control unit (not shown) through handle 112 through attachment plate 116 via one or more of the ports disposed therein and to cooling head 114. After flowing through cooling head 114, the heat transfer fluid may then complete the closed loop by flowing through attachment plate 116 via one or more of the ports disposed therein through handle 112 and back to control unit 100.

In the embodiment shown, handle 112 has a cylindrical-type shape to accommodate positioning in a user's hand. However, various other sizes and shapes may be utilized to form handle 112, such as being mounted to a strap, having a shape similar to a pistol grip, having an elongated shaft, and/or other geometric and/or ergonomic shape. Handle 112 may be formed from or may include an insulating material capable of insulating the outside of handle 112 from the temperature of the fluid flowing therethrough. For example, in one embodiment, handle 112 made be formed of ABS plastic. In some embodiments, handle 112 may be formed of two pieces coupled together having tubes and/or channels running therethrough. In some embodiments, handle 112 may be symmetrical so that halves of handle 112 may be formed from a same injection mold. In various embodiments, handle 112 may be formed of a single piece of material. In some embodiments, heat-transfer fluid does not flow through handle 112, rather one or more flow paths of the heat-transfer fluid may flow around handle 112 to cooling head 114. Various embodiments of contact cooler 102 may include more or less parts than the embodiment shown. Similarly, the various parts of contact cooler 102 may be coupled together in a plurality of ways including, but not limited to, screws, adhesive, welding, brads, rivets, snaps, clips or any other suitable way of construction.

FIG. 3A is a top view of cooling head 114. In the embodiment shown, cooling head 114 includes a plurality of screw holes 122 for receiving a plurality of screws, a flow channel 124, and flow ports 126 for flow of heat-transfer fluid therethrough. In various embodiments, screw holes 122 may be disposed around a periphery of cooling head 114 for receiving screws to facilitate the coupling of the handle (not shown) and the attachment plate (not shown) thereto. In various embodiments, the flow ports of the attachment head may align with flow ports 126 to facilitate the heat-transfer fluid flow into and out of cooling head 114. After entering a first flow port of flow ports 126, the heat-transfer fluid flows through flow channel 124 and exits a second flow port of flow ports 126. In various embodiments, o-ring 118 may be disposed between the attachment plate and cooling head 114. In some embodiments, o-ring 118 may have a diameter substantially equal to the diameter of flow channel 124 and may have a width on the order of width 124a. In that way, o-ring 118 may be adapted to be partially disposed within flow channel 124. Flow channel 124 may be of any shape or size such as, for example, a circle, an oval, a square, a rectangle, or any other geometric shape. By way of example, flow channel 124 is shown in FIG. 3A as being roughly circular.

In similar fashion, FIG. 3B depicts a bottom view of cooling head 114. For the sake of clarity, an outer covering is not shown in FIG. 3B. The location of a heat transfer surface 128 relative to flow channel 124 is depicted as a dashed line. The remaining structures depicted in FIG. 3B are substantially similar to those described above with respect to FIG. 3A. However, it should noted that, while flow channel 124 was depicted by way of example in FIG. 3A as being roughly circular, flow channel 124 is depicted, again by way of example, in FIG. 3B as having an oval shape.

FIGS. 3C-D are cutaway side views of various embodiments of cooling head 114 along line A-A of FIG. 3A. In FIG. 3C, a depth of flow channel 124 can be seen relative to a depth of cooling head 114. Similarly, a depth of screw holes 122 can also be seen. In various embodiments, the depths of flow channel 124 and screw holes 122 may be larger or smaller depending on user preferences. In various embodiments, the depth of flow channel 124 may be varied to vary the heat-transfer properties of cooling head 114. For example, a deeper flow channel 124 may allow a temperature of a heat-transfer surface on a lower portion of cooling head 114 to be varied more quickly than a shallower flow channel.

In similar fashion, FIG. 3D is a cutaway side view of an additional embodiment of cooling head 114 along line A-A of FIG. 3A. A depth of flow channel 124 can be seen relative to a depth of cooling head 114. However, screw holes 122 are not explicitly shown in FIG. 3D. As shown in FIG. 3D, in some embodiments, flow channel 124 is contoured to follow the shape of cooling head 114. Such a feature ensures constant spacing between flow channel 124 and heat transfer surface 128 of cooling head 114. This constant spacing ensures that, during use, heat transfer surface 128 has no noticeable variation in temperature across its surface. In other words, the formation of "hot spots" or "cold spots" on heat transfer surface 128 is prevented. Other structures of FIG. 3D are substantially similar to those described above with respect to FIG. 3C.

Figure 3E:
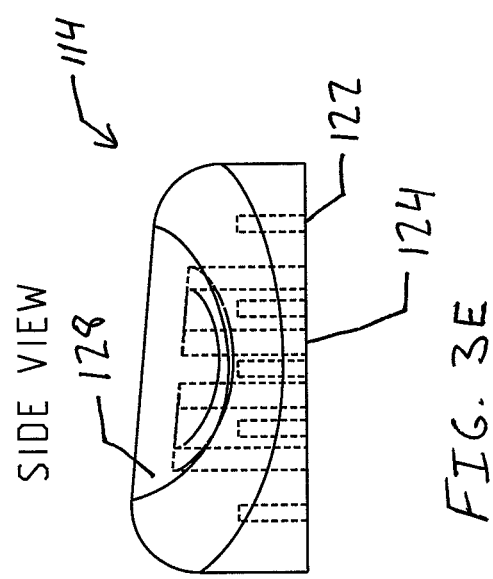
FIG. 3E is a side view of the contact cooling head of FIG. 3D.

FIG. 3E is a side view of cooling head 114. A depth of flow channel 124 can be seen relative to a depth of cooling head 114. Similarly, a depth of screw holes 122 can also be seen. In addition, the placement of heat-transfer surface 128 relative to flow channel 124 is also illustrated. As described above with respect to FIG. 3C, the depths of flow channel 124 and screw holes 122 may be larger or smaller depending on user preferences. In various embodiments, the depth of flow channel 124 may be varied to vary the heat-transfer properties of cooling head 114. For example, a deeper flow channel 124 may allow a temperature of a heat-transfer surface on a lower portion of cooling head 114 to be varied more quickly than a shallower flow channel.

Figure 3F:
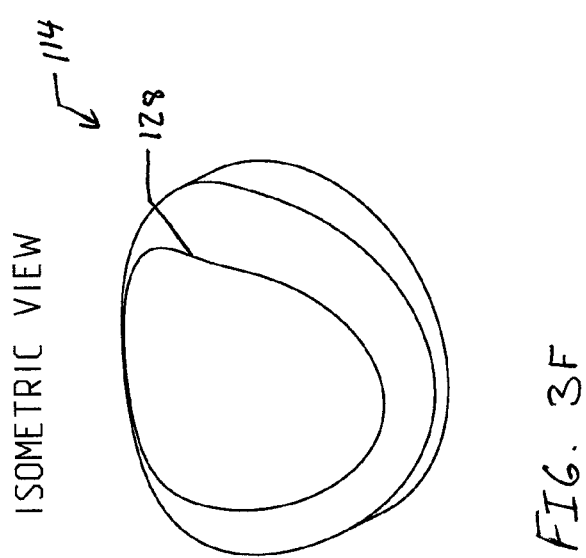
FIG. 3F is an isometric view of the contact cooling head of FIG. 1.

FIG. 3F is an isometric view of cooling head 114 showing the placement of heat-transfer surface 128.

Figure 4C:
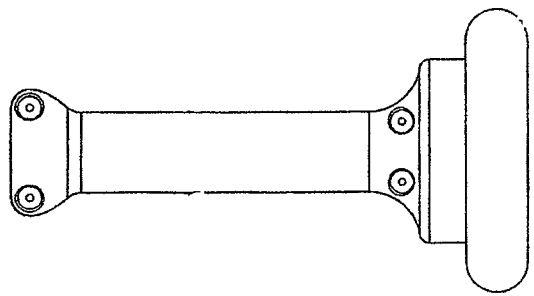
FIGS. 4A-4C are side views of various embodiments of a contact cooling head.
Figure 4B:
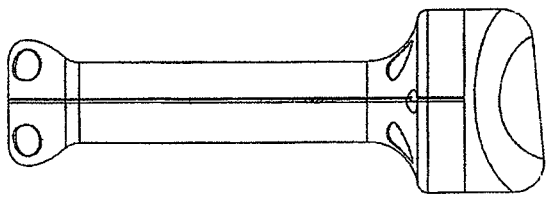
Figure 4A:
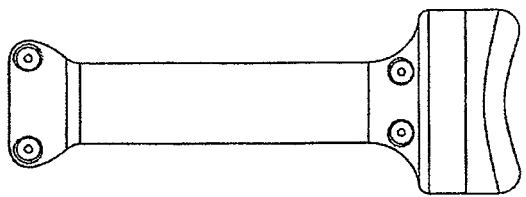

FIGS. 4A-4C show various embodiments of contact cooler 102 having a variety of different shapes. FIG. 4A shows contact cooler 102a having a concave heat-transfer surface. FIG. 4B shows contact cooler 102b having a convex heat-transfer surface. FIG. 4C shows a contact cooler 102c having a flat heat-transfer surface. While three contact coolers 102a-102c having different shapes are shown in FIGS. 4A-4C, contact cooler 102 may have a heat-transfer surface of any shape and/or size. The various sizes and shapes of the various heat-transfer surfaces may be designed to be used for various purposes and for contacting various surfaces. For example, a concave head, such as contact cooler 102a, may be ideal for use on areas such as along a shin bone, while a convex head, such as contact cooler 102b, may be preferable for use on a face or neck of a patient. Similarly, a head having a relatively large flat surface, such as contact cooler 102c, may be preferable when cooling a back or chest region.

Figure 5C:
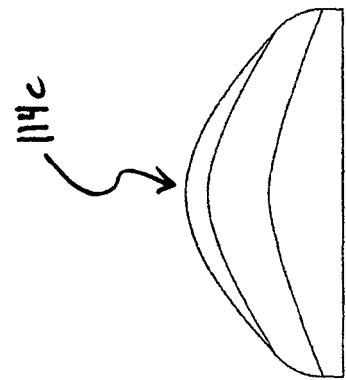
FIGS. 5A-5C are side views of contours of various embodiments of a contact cooling head.
Figure 5B:
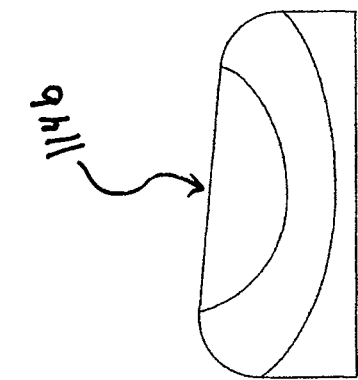
Figure 5A:
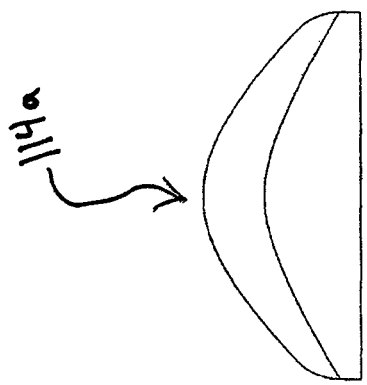

FIGS. 5A-5C show various embodiments of cooling head 114 having a variety of different convex shapes. FIG. 5A shows cooling head 114a having a convex shape. FIG. 5C shows cooling head 114b having a relatively flat convex shape. FIG. 5c shows cooling head 114c having a relatively deep convex shape. FIGS. 5A-5C illustrate that a plurality of different size and shapes may be utilized for cooling head 114 depending on desired heat transfer characteristics and the characteristics of a surface to be contacted. The efficacy of use of the cooling head 114 is thus increased by select sizes and shapes of the cooling head for select patient treatment applications.

Figure 6:
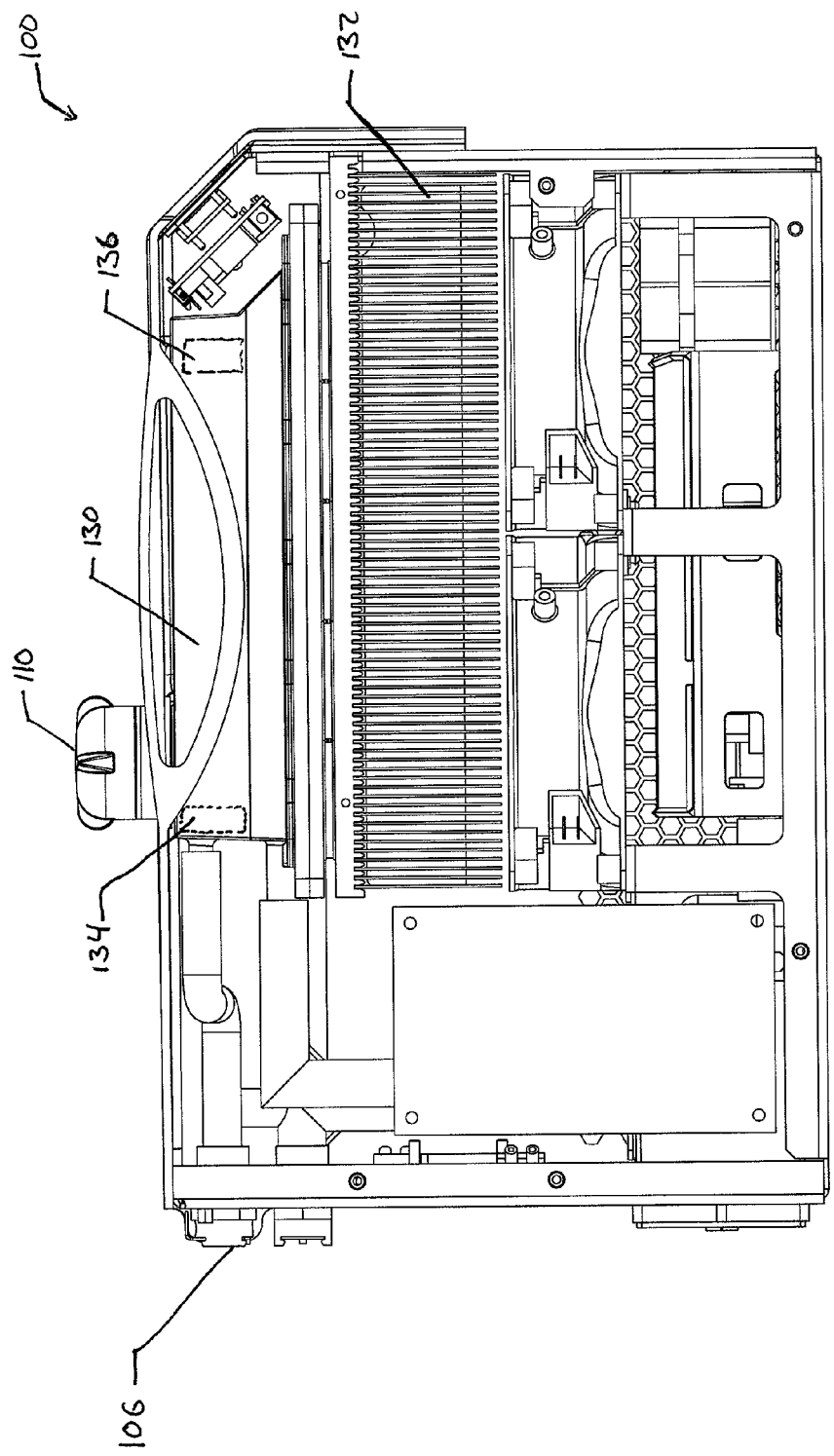
FIG. 6 is a side view of a cutaway of a control unit.

FIG. 6 is a side cutaway view of control unit 100. Control unit 100 includes input and output ports 106 disposed on a back side thereof. Input and output ports 106 are in fluid communication with a reservoir 130 having refill opening 110 for adding and/or removing heat transfer fluid therefrom. Reservoir 130 may be adapted to hold an amount of heat-transfer fluid. A heat-transfer assembly (HTA) 132 may be disposed relative to reservoir 130 and in thermal communication therewith. HTA 132 may include a plurality of thermoelectric coolers (TEC) operable to actively heat or cool the heat-transfer fluid in reservoir 130. Control unit 100 may be adapted to run on AC or DC power and may include circuitry allow the unit to be used in a plurality of different countries, such as, for example, the United States, the United Kingdom, and/or other countries.

A first sensor 134 may be disposed relative to a first portion of reservoir 130 and adapted to monitor a temperature of the heat-transfer fluid near an input of reservoir 130. A second sensor 136 may be disposed relative to a second portion of reservoir 130 and adapted to monitor a temperature of the heat-transfer fluid near an output of reservoir 130. First and second sensors 134 and 136 may be located at any appropriate location to measure the temperature of heat-transfer fluid entering and leaving control unit 100. In some embodiments, first sensor 134 may be located near an input of reservoir 130 and second sensor 136 may be located near an output of reservoir 130. In other embodiments first and second sensors 134 and 136 may be located near respective input and output ports 106 on control unit 100. Additionally, in some embodiments, additional sensors (not shown) may be employed to measure the temperature of the heat transfer fluid at any desired point in reservoir 130 or control unit 100. As will be explained in more detail below, in some embodiments, the difference between the temperatures measured by first sensor 134 and second sensor 136 may be utilized to calculate the temperature at the heat-transfer surface of the cooling head of the contact cooler (not shown) and may also be used to monitor various conditions such as when the contact cooler is contacting a hot surface, such as a skin surface of a patient.

Figure 7:
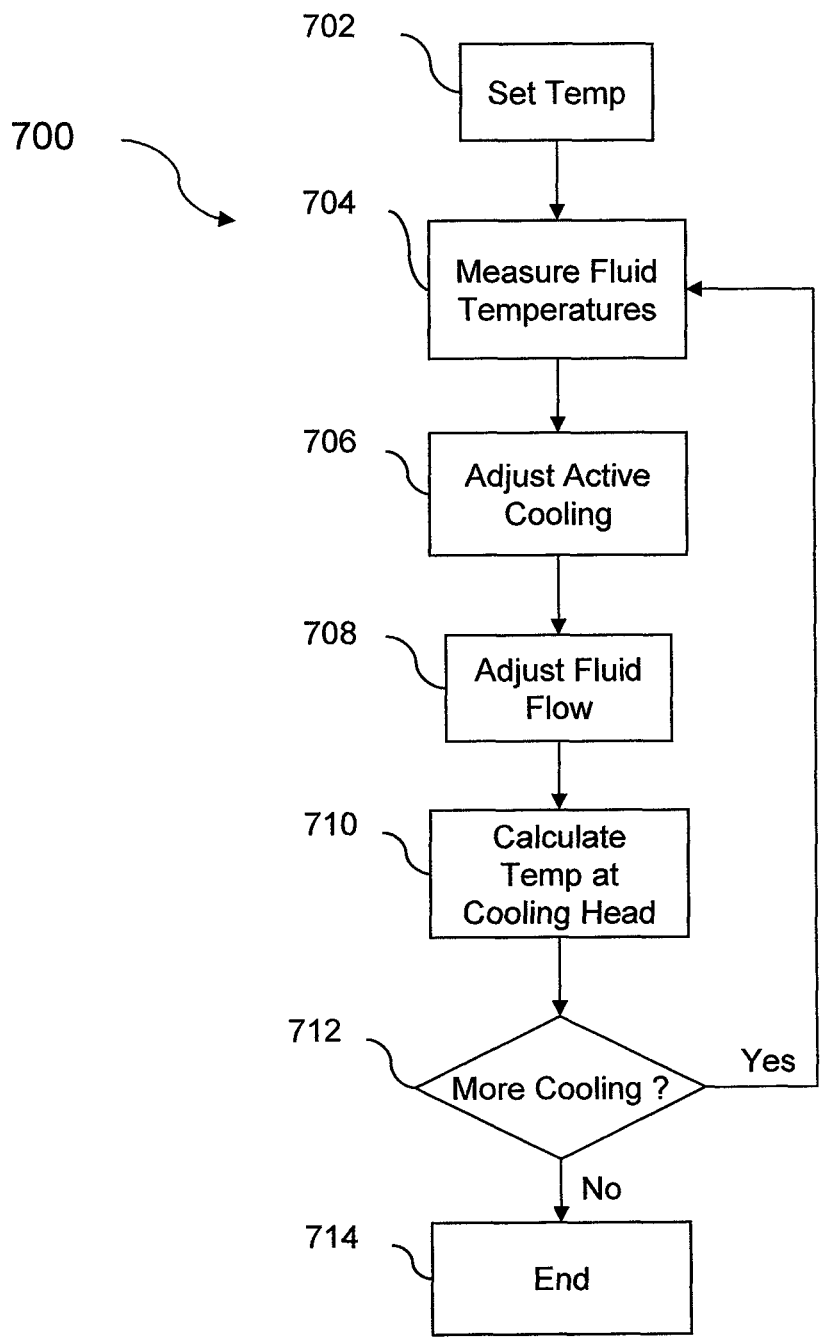
FIG. 7 is a process flow diagram illustrating a method for heating and/or cooling a surface via a contact cooler.

FIG. 7 is a flowchart showing an embodiment of a method 700 for heating and/or cooling a surface via a contact cooler. For descriptive purposes, the following description refers only to cooling, but in various embodiments, the method also includes heating. Method 700 begins at step 702 when a user activates a control unit either by turning the control unit on from an off position, activating the control unit from a standby position, and/or inputs an input operable to activate the system. At step 702, the user indicates a Set Temp, which may be a temperature to which the user desires the control unit to cool and/or heat a cooling head. In some embodiments, the user may input or select a mode of operation and/or other parameters and the control unit may automatically select a temperature based on the user input. At step 704, a temperature of the heat transfer fluid is measured. In some embodiments, a first temperature is measured at an input of the reservoir and a second temperature is measured at an output of the reservoir. In various embodiments, a plurality of sensors may be utilized to measure various temperatures, such as, for example, the temperature of a cold plate disposed between the TEC and the fluid reservoir may be measured. Before active cooling and/or fluid flow begins, the difference between the first and second temperatures may be minimal.

At step 706, control signals are sent to one or more HTAs to begin actively cooling heat transfer fluid disposed in a reservoir inside the control unit. As will be described in more detail below, to reduce the time to reach Set Temp while also reducing overshoot, the amount of active cooling will depend on the difference between the temperature of the heat transfer fluid and the Set Temp. At step 708, control signals are sent to a fluid pump to begin flowing the heat transfer fluid from the reservoir through a closed loop circuit to and from the contact cooler via connectors coupled to the control unit and back to the reservoir. In various embodiments, the control unit may begin to flow the heat transfer fluid before actively cooling the heat transfer fluid. In various embodiments, the rate of fluid flow is monitored.

At step 710, the temperature at a cooling surface of the contact cooler is calculated based in at least partial dependence on the difference between the first and second temperatures and various thermal properties of the contact cooler. If more cooling time is needed, the method continues monitoring the temperatures, adjusting the active cooling, and adjusting the flow rate. If cooling is no longer needed, the method proceeds to step 714 and ends.

In various embodiments, the temperature of the cooling surface is not directly measured, but rather is calculated at step 710 based on the difference between the first and second temperatures. In various embodiments, a plurality of known properties may be utilized to increase the accuracy of the calculation, such as, for example a diameter of the connector coupling the control unit to the contact cooler, the properties of the cooling head are known, such as, for example, the volume inside the cooling head, the thermal properties of the cooling head, the thickness between the flow channel and the cooling surface, and/or other properties. For example, the temperature may be calculated using a moving average computation to determine the temperature of the cooling surface. In some embodiments, the first and second derivatives of the temperature difference may be utilized to calculate the rate and acceleration factors for the temperature. This information may be used in a feed back loop to determine the amount of active cooling needed and to reduce overshoot.

For example, a stable state may be identified when the temperature of the heat-transfer fluid exiting the reservoir is substantially equal to the Set Temp and the difference between the first and second temperatures is minimal. In the stable state, active cooling of the reservoir may cease as long as the exit temperature of the heat transfer fluid continues to be within a predetermined range of the Set Temp, for example within +/−0.25 C.°. In some embodiments, the cooling algorithm may be able to maintain a steady state temperature at the cooling surface to within +/−0.1 C.° of coolant set temperature.

A slow-cool state or control-drive state may be identified when the exit temperature is substantially equal to the Set Temp, but there is a difference between the first temperature and the second temperature and the amount of active cooling of the reservoir may be lowered. In the control-drive state, the amount of active cooling may be proportional to the temperature difference. This is a unique way to achieve a quick settling time. As the temperature of the heat transfer fluid nears the Set Temp, the magnitude of the difference will also decrease. Due to the linear relationship between the temperature difference and the amount of active cooling, the amount of active cooling will reduce as the difference lessens. This may dampen any temperature overshoot and minimize temperature oscillations at set point. Minimizing overshoot may be desirable when cooling a cooling surface to a temperature at or near 0° C. because overshooting would lower the temperature of the cooling surface to below 0° C. and potentially causing damage and/or irritation to a skin surface.

A fast-cool state or max-drive state may be identified when the exit temperature is outside a predetermined range of the Set Temp, for example more than +/−2.00° C. During the fast-cool state, a maximum amount of active cooling may be applied to the reservoir. This mode may be used to provide rapid response to changing Set Temps or thermal conditions.

In various embodiments, within each state, a cooling algorithm may be operable to utilize the measured difference between the first and second temperatures over a period of time to calculate the first and second derivatives of the temperature changes. The first derivative may be utilized to calculate at what rate the temperature is changing and the amount of active cooling and/or flow rate may be adjusted accordingly to reduce the likelihood of overshooting the Set Temp. For example, if the system is in a stable state or a control-drive state, an optimization loop may be utilized to monitor the average temperature difference over a given time interval in order to increase accuracy. The level of adjustment may be determined by the magnitude of the error and rate of change of the error (first derivative).

The second derivative may be utilized to detect sudden temperature changes, such as for example, temperature spikes. When a temperature spike is detected, the cooling algorithm may be adapted to maintain a previous state until the transient event has passed. By detecting temperature spikes, the cooling algorithm may be able to minimize temperature oscillations at the cooling surface.

In one embodiment, a plurality of cooling heads are designed with similar heat transfer characteristics so that a user may switch between various cooling heads and the algorithm for calculating the temperature at the cooling surface of the cooling head will not have to be changed. In another embodiment, several algorithms may be used depending on which contact cooling head is being used. For example, if a thick contact cooling head is being used, the control unit would use an algorithm that would accurately calculate the surface temperature based on the inflow and outflow temperatures of the heat transfer fluid. Similarly, if a cooling head comprising a first material, for example stainless steel, is switched with a cooling head comprising a second, different material, for example, polished aluminum, a different algorithm would be used to calculate the temperature at the surface of the cooling head comprising the second material than was used to calculate the temperature at the contact surface of the cooling head comprising the first material. In one embodiment, a user can input which cooling head is being used into the control unit. In another embodiment, a user can input various characteristics of the cooling head being used and the control unit will select an algorithm that best approximates the cooling head being used. In still other embodiments, the control unit may identify which head is being used and select an algorithm accordingly. For example, if each head contained an RFID tag, the control unit could then monitor which cooling head was being utilized. In still other embodiments, the cooling head may be coupled to the control unit in any manner capable of identifying various characteristics of the head to the control unit. In some embodiments, a barrier may be disposed in between the cooling head and the contact surface for sanitary purposes. Various plastic or latex-free covers could be used such as a fluid impermeable plastic such as polyethylene, polyvinylchloride, or other similar material. The control unit may update the algorithm used to reflect the changes caused by such a barrier if needed.

The shape, size, material, and other characteristics of a contact cooler may be adapted for a variety of different uses. In some embodiments, the contact cooler may be utilized to cool a skin surface of a patient. The skin cooling may anesthetize the surface thereby reducing pain sensations caused by various medical procedures. For example, an area may be cooled, for example, 20 seconds, prior to a shot or injection being administered and may be cooled, for example, 20 seconds, after the shot or injection. The cooling before the shot may reduce pain caused by the shot and the cooling after may reduce swelling. In some embodiments, an area may be cooled prior to a tattoo removal process being commenced. In some embodiments, an area may be cooled prior to a laser-hair removal process being commenced. In some embodiments, an area may be cooled prior to a fat or lipid moving process or fat reduction process being commenced.

In some embodiments, a contact cooler may include an attachment adapted to facilitate use of the contact cooler in conjunction with other devices. For example, in various embodiments, the contact cooler may include protrusions disposed along a side of the contact cooler and adapted to mate with a laser, such as an intense pulse light. In that way, cooling may be provided at the same time a laser treatment is being provided. Integrating the contact cooler and another device into a single apparatus may facilitate manual manipulation of the devices.

From the foregoing detailed description of specific embodiments of the invention, it should be apparent that a system for contact cooling a surface that is novel has been disclosed. Although specific embodiments of the invention have been disclosed herein in some detail, this has been done solely for the purposes of describing various features and aspects of the invention, and is not intended to be limiting with respect to the scope of the invention. It is contemplated that various substitutions, alterations, and/or modifications, including but not limited to those implementation variations which may have been suggested herein, may be made to the disclosed embodiments without departing from the spirit and scope of the invention as defined by the appended claims which follow.

What is claimed is:

1. A system for thermally conditioning a surface, the system comprising:
    a control unit comprising a fluid reservoir disposed therein, the fluid reservoir comprising an input and an output operable to allow circulation of a heat transfer fluid therethrough;
    a contact cooler comprising:
    a handle;
    an attachment plate operatively coupled to the handle;
    a cooling head operatively coupled to the attachment plate, the cooling head comprising a flow channel disposed therein, the flow channel fluidly coupled to the fluid reservoir, wherein a flow channel path defines a plane generally orthogonal to a longitudinal axis of the cooling head; and
    an o-ring disposed between the flow channel and the attachment plate, the o-ring comprising a diameter substantially equal to a diameter of the flow channel;
    a first sensor disposed at the input of the fluid reservoir, the first sensor operable to measure a first temperature of the heat transfer fluid entering the fluid reservoir;
    a second sensor disposed at the output of the fluid reservoir, the second sensor operable to measure a second temperature of the heat transfer fluid leaving the fluid reservoir; and
    wherein, responsive to a difference between the first temperature and the second temperature, the control unit is operable to heat or cool the heat transfer fluid in the fluid reservoir so as to maintain a constant temperature at the contact cooler.

2. The system of claim 1 further comprising a heat transfer assembly disposed within the control unit and thermally coupled to the fluid reservoir.

3. The system of claim 2, wherein the heat transfer assembly comprises at least one thermoelectric cooling device operable to actively thermally condition the heat transfer fluid.

4. The system of claim 1, wherein the path of the flow channel comprises a shape selected from a group of geometric shapes comprising circle, oval, square, and rectangle.

5. The system of claim 1, wherein placement of the flow channel relative to an exterior surface of the contact cooler varies heat transfer properties of the contact cooler.

6. A method for providing therapeutic heating or cooling of a bodily surface, the method comprising:
    providing a thermal conditioning system comprising a reservoir for a heat transfer fluid disposed therein;
    setting a desired temperature of a contact cooler, the contact cooler having a cooling head;
    circulating the heat transfer fluid from the reservoir through the contact cooler, via a flow channel disposed in the cooling head, the flow channel defining a plane generally orthogonal to a longitudinal axis of the cooling head;
    measuring a first temperature of the heat transfer fluid at an input of the reservoir;
    measuring a second temperature of the heat transfer fluid at an output of the reservoir;
    calculating, based upon the first temperature and the second temperature, a rate of temperature change and a temperature acceleration factor at the contact cooler; and
    heating or cooling the heat transfer fluid in the reservoir responsive to at least one of the rate of temperature change and the temperature acceleration factor.

7. The method of claim 6, wherein the heating or cooling the heat transfer fluid comprises heating or cooling the heat transfer fluid via a heat transfer assembly thermally coupled to the reservoir.

8. The method of claim 7, wherein the heat transfer assembly comprises a thermoelectric cooling unit.

9. The method of claim 6, wherein the calculating comprises employing a moving average computation.

10. The method of claim 6, wherein the calculating comprises calculating, via a first and second derivative of a difference between the first and second temperatures, a rate factor and an acceleration factor.

11. The method of claim 6, further comprising applying, via the contact cooler comprising a convex-shaped head, therapeutic heating or cooling to a face or neck of a patient.

12. The method of claim 6, further comprising applying, via the contact cooler comprising a concave-shaped head, therapeutic heating or cooling to a leg or arm of a patient.

13. The method of claim 6, further comprising applying, via the contact cooler comprising a substantially flat head, therapeutic heating or cooling to a chest or back of a patient.

14. A method for heating or cooling a bodily surface, the method comprising:
    indicating a desired temperature of a contact cooler, the contact cooler having a cooling head;
    measuring a starting temperature of a heat transfer fluid contained in a fluid reservoir;

heating or cooling the heat transfer fluid responsive to a difference between the desired temperature of the contact cooler and the starting temperature of the heat transfer fluid;

circulating the heat transfer fluid through the contact cooler in a closed-loop circuit, via a flow channel disposed in the cooling head, the flow channel defining a plane generally orthogonal to a longitudinal axis of the cooling head;

measuring a first temperature of the heat transfer fluid at an input of the fluid reservoir and a second temperature of the heat transfer fluid at an output of the fluid reservoir;

calculating, based upon a difference between the first temperature and the second temperature, at least one of an actual temperature of the contact cooler, a rate of temperature change of the contact cooler, and a temperature acceleration factor associated with the contact cooler; and heating or cooling the heat transfer fluid in the fluid reservoir responsive to at least one of the rate of temperature change, a rate of temperature difference between the actual temperature of the contact cooler and the desired temperature of the contact cooler, and the temperature acceleration factor.

15. The method of claim 14, wherein the actual temperature of the contact cooler is not directly measured.

16. The method of claim 14, further comprising maintaining a steady-state temperature at the contact cooler to within +/−0.1° C. of the desired temperature of the contact cooler.

17. The method of claim 14, further comprising identifying a stable state when the second temperature is substantially equal to the desired temperature of the contact cooler and the difference between the first temperature and the second temperature is minimal.

18. The method of claim 14 further comprising identifying a slow-cool state when the second temperature is substantially equal to the desired temperature of the contact cooler and the difference between the first temperature and the second temperature is non-zero.

19. The method of claim 14, further comprising identifying a fast-cool state when the second temperature is outside of a pre-determined range of the desired temperature of the contact cooler.

20. A method for providing therapeutic heating or cooling of a bodily surface of a patient, the method comprising:

providing a thermal conditioning system comprising a reservoir for a heat transfer fluid disposed therein;

providing a contact cooler, the contact cooler comprising:
a handle;
an attachment plate operatively coupled to the handle;
a cooling head operatively coupled to the attachment plate, the cooling head comprising a flow channel disposed therein, the flow channel fluidly coupled to the fluid reservoir, wherein a flow channel path defines a plane generally orthogonal to a longitudinal axis of the cooling head; and
an o-ring disposed between the flow channel and the attachment plate, the o-ring comprising a diameter substantially equal to a diameter of the flow channel;

setting a desired temperature of the contact cooler;
circulating the heat transfer fluid from the reservoir through the contact cooler; and
heating or cooling the heat transfer fluid for treatment of the patient.

* * * * *